(12) United States Patent  (10) Patent No.: US 7,773,228 B1
Hollingsworth et al.  (45) Date of Patent: Aug. 10, 2010

(54) SURFACE PLASMON NONCONTACT ELECTRIC FIELD SENSORS AND RELATED METHODS

(75) Inventors: Russell E. Hollingsworth, Arvada, CO (US); Bruce Roy Lanning, Littleton, CO (US)

(73) Assignee: ITN Energy Systems, Inc., Littleton, CO (US)

( * ) Notice: Subject to any disclaimer, the term of this patent is extended or adjusted under 35 U.S.C. 154(b) by 176 days.

(21) Appl. No.: 12/190,419

(22) Filed: Aug. 12, 2008

Related U.S. Application Data (60) Provisional application No. 60/956,103, filed on Aug. 15, 2007.

(51) Int. Cl.
G01N 21/55 (2006.01)
G01J 1/58 (2006.01)
G02B 1/10 (2006.01)

(52) U.S. Cl. .............. 356/445; 250/461.2; 250/338.1; 359/245; 359/585

(58) Field of Classification Search ......... 356/445–448; 250/461.2, 338.1, 234–236; 359/585, 578, 359/245, 247
See application file for complete search history.

(56) References Cited

U.S. PATENT DOCUMENTS

| | | | |
|---|---|---|---|
| 4,765,705 A | 8/1988 | Seymour et al. | |
| 5,115,336 A * | 5/1992 | Schildkraut et al. | 359/263 |
| 5,633,492 A * | 5/1997 | Nikitin et al. | 250/214 R |
| 5,759,745 A * | 6/1998 | Hollingsworth | 430/313 |
| 6,649,901 B2 | 11/2003 | Thio et al. | |
| 6,667,807 B2 * | 12/2003 | Lieberman | 356/445 |
| 6,782,179 B2 * | 8/2004 | Bozhevolnyi et al. | 385/131 |
| 6,834,027 B1 | 12/2004 | Sakaguchi et al. | |
| 6,871,084 B1 | 3/2005 | Kingsley et al. | |
| 6,982,819 B2 * | 1/2006 | Sawin et al. | 359/245 |
| 6,992,826 B2 * | 1/2006 | Wang | 359/585 |
| 7,057,151 B2 | 6/2006 | Lezec et al. | |
| 7,176,450 B2 | 2/2007 | Hollingsworth | |
| 7,250,598 B2 | 7/2007 | Hollingsworth et al. | |
| 7,456,972 B2 * | 11/2008 | Ke et al. | 356/445 |
| 7,511,285 B2 * | 3/2009 | Bernstein | 250/461.2 |
| 2004/0190116 A1 | 9/2004 | Lezec et al. | |
| 2004/0211901 A1 | 10/2004 | Syllaios et al. | |
| 2008/0185521 A1 | 8/2008 | Hollingsworth | |

OTHER PUBLICATIONS

Bulmer, C.H., "Sensitive, highly linear lithium niobate interferometers for electromagnetic field sensing", Appl. Phys. Lett. 53(24), Dec. 12, 1988, pp. 2368-2370.

(Continued)

*Primary Examiner*—Sang Nguyen
(74) *Attorney, Agent, or Firm*—Lathrop & Gage LLP (57) ABSTRACT

A surface-plasmon electric field sensor has a plasmonic portion having an electro-optic dielectric material coated on one side with a transparent conductive layer and on another side with a thin layer of conductive metallic layer. The metallic layer has alternating grating and smooth regions, the smooth regions being of length near a multiple of an effective wavelength of the light in the electro-optic layer, and the grating regions having lines on a pitch near the effective wavelength. The sensor has a light source for illuminating the plasmonic portion with plane-polarized light having a free-space wavelength and a photodetector.

30 Claims, 4 Drawing Sheets

OTHER PUBLICATIONS

Burstein, E., "Surface polaritons—propagating electromagnetic modes at interfaces", vol. 11, No. 6, Nov./Dec. 1974, pp. 1004-1019.

Devaux et al., "Launching and decoupling surface plasmons via micro-gratings", Appl. Phys. Lett., vol. 83, No. 24, Dec. 15, 2003, pp. 4936-4938.

Ditlbacher, H. et al., "Two-dimensional optics with surface plasmon polaritons", Appl. Phys. Lett., vol. 81, No. 10, Sep. 2, 2002, pp. 1762-1764.

Ebbesen et al., "Extraordinary optical transmission through subwavelength hole arrays", Nature, vol. 391, Feb. 12, 1998, pp. 667-669.

Flammer, P.D. et al., "Theoretical study of enhanced transmission through subwavelength linear apertures flanked by periodic corrugations", Proc. of SPIE, vol. 6323, Aug. 13-16, 2006, 12 pages.

Flammer, P.D. et al., "Interference and Resonant Cavity Effects Explain Enhanced Transmission Through Subwavelength Apertures in Thin Metal Films", submitted to physical review letters on Jul. 7, 2006, pp. 1-5.

Lezec et al., "Beaming light from a subwavelength aperture", Science, vol. 297, Aug. 2, 2002, pp. 820-822.

Lezec et al., "Diffracted evanescent wave model for enhanced and suppressed optical transmission through subwavelength hole arrays", Optics Express, vol. 12, No. 16, Aug. 9, 2004, pp. 3629-3651.

Maier et al., "Electromagnetic energy transport below the diffraction limit in periodic metal nanostructures", Proc. of SPIE vol. 4456, Dec. 5, 2001, pp. 22-30.

Mills, J.D., "Evanescent field imaging of an optical fiber Bragg grating", Applied Physics Letters, vol. 75, No. 26, Dec. 27, 1999, pp. 4058-4060.

Nomura et al., "Nanodot coupler with a surface plasmon polariton condenser for optical far/near-field conversion", Appl. Phys. Lett., vol. 86, No. 18, May 2, 2005, 3 pages.

Paloczi et al., "Replica-molded electro-optical polymer Mach-Zehnder modulator", Appl. Phys. Lett., vol. 8, No. 10, Sep. 6, 2004, pp. 1662-1664.

Ritchie, R.H., "Surface plasmons in solids", Surface Science, vol. 34, No. 1, Jan. 1973, pp. 1-19.

Rost, R.C. et al., "Deposition and analysis of lithium niobate and other lithium niobium oxides by rf magnetron sputtering", Journal of Applied Physics, vol. 72, No. 9, Nov. 1, 1992, pp. 4336-4343.

Sarid, D., "Long range surface-plasma waves on very thin metal films", Physical Review Letters, vol. 47, No. 26, Dec. 28, 1981, pp. 1927-1930.

Schick, I.C. et al., "Experimental study of enhanced transmission through subwavelength linear apertures flanked by periodic corrugations", Proc. of SPIE vol. 6323, Aug. 13-16, 2006, 12 pages.

Smolyaninov, Igor I., "Experimental study of surface-plasmon scattering by individual surface defects", Physical Review B, vol. 56, No. 3, Jul. 15, 1997, pp. 1601-1611.

Office Action issued in U.S. Appl. No. 11/671,122, dated Apr. 15, 2009, 17 pages.

Response to Office Action filed is U.S. Appl. No. 11/671,122 dated Jul. 15, 2009, 20 pages.

* cited by examiner

SURFACE PLASMON NONCONTACT ELECTRIC FIELD SENSORS AND RELATED METHODS

CROSS REFERENCE TO RELATED APPLICATIONS

This application claims benefit of priority to U.S. Provisional Patent Application Ser. No. 60/956,103 filed 15 Aug. 2007, which is incorporated herein by reference.

BACKGROUND

Biological Applications

Typically, biological electrical signals, such as electroencephalographic (EEG), electromyographic (EMG), and electrocardiographic (ECG) signals, are sensed with contact electrodes.

Contact electrodes typically require a moist, electrically conductive, paste be present between the electrode and skin surface in order to maintain low contact resistance. This paste, and associated contact electrodes, can cause difficulties ranging from allergic contact dermatitis and skin staining to intermittent connections as the paste dries. Contact electrodes may require skin be abraded during attachment, causing discomfort and irritation, and callus formation if frequently repeated. Open circuits often result as electrodes shift due to patient movement. Electrodes must also be either disposable, or carefully cleaned between patients to avoid transmission of infection.

Many electrodes are typically required for such applications as EEG and polysomnography, requiring much time and care to attach to patients in correct patterns. Even the classical "12-lead" ECG commonly used in medical practice requires that a dozen electrodes be attached to the patient.

The problems of contact electrodes are aggravated by long-term use. Polysomnography requires patients be wired for EEG, EMG, and ECG signals for a full night's sleep of at least 6 hours; Holter monitors typically require at least 24 hours of ECG monitoring; and patients may desire to wear EMG-controlled prosthetics as much as 18 hours a day for months or years. It may be useful to monitor epileptics for seizure activity or sub-seizure EEG disturbances over periods of weeks while medication doses are adjusted. Such long term use gives ample opportunity for contact dermatitis with contact electrodes, especially in those people who are already sensitized to metals such as nickel or silver.

Experiments have shown the possibility of using EEG signals to control assistive devices for the severely handicapped, and suggestions have been made that there may be a market for EEG-controlled toys or computer games. Long term use of contact electrodes with conductive gels is undesirable in these applications.

It is therefore desirable to have noncontact sensors for microvolt and millivolt-level electrical field signals that do not require use of the traditional conductive gel or paste between sensor and skin.

A Mach-Zehnder interferometer fabricated on a lithium niobate substrate has been used for non contact or minimal-contact, high-impedance, electric field sensing, as described in U.S. Pat. No. 6,871,084. A conductive rubber pad with a saw tooth surface was used with this sensor to contact the scalp through the hair for EEG monitoring, while the larger ECG signals were measured through light clothing with no direct skin contact. This is, however, a fairly large and complex device, and was of marginal sensitivity for EEG signals.

Surface Plasmon Sensing

The Surface Plasmon effect involves electromagnetic radiation propagating as quantized collective oscillations of the "free electron gas" of a metal along a metal-dielectric interface, where these free electron gas oscillations can couple to photons as "polaritons". Such coupled radiation can be guided by structures as small as 10% of the free-space wavelength of the electromagnetic radiation.

The propagation of surface plasmons is sensitive to a variety of surface-related effects, including changes to the local index of refraction of adjacent materials. This effect has been used in sensors that measure characteristics of proteins bound to a metal surface.

Surface plasmons at a metal-dielectric boundary can be excited in the Kretchmann-Raether configuration by directing a beam of light through the dielectric onto the boundary at an angle such that most incident light is reflected. Surface plasmons can also be created by guiding electromagnetic radiation through a tapered waveguide of dielectric adjacent to the metal.

Electromagnetic radiation also couples to surface plasmons where a grating on the metal surface has dimensions on the order of a wavelength of the radiation, as described in U.S. Pat. No. 4,765,705. Similar structures can also couple energy from plasmons back into electromagnetic radiation. Gratings on the metal surface of appropriate dimensions, such as a grating having spacing equal to a multiple of half a wavelength, can also reflect plasmons.

It is known that certain electro-optic materials, such as lithium niobate crystals, have an index of refraction that varies with an applied electric field.

SUMMARY

In one embodiment, a surface-plasmon electric field sensor has a plasmonic portion having an electro-optic dielectric material coated on one side with a transparent conductive layer and on another side with a thin layer of conductive metallic layer. The metallic layer has alternating grating and smooth regions, the smooth regions being of length near a multiple of an effective wavelength of the light in the electro-optic layer, and the grating regions having lines on a pitch near the effective wavelength. The sensor has a light source for illuminating the plasmonic portion with plane-polarized light having a free-space wavelength and a photodetector.

In one embodiment, a garment, having a skinward side and an outside side, includes a plurality of sensors disposed to sense electric fields at the skinward side of the garment. Each sensor has a light source for emitting plane-polarized light having a free-space wavelength, a photodetector, and a plasmonic portion. The plasmonic portion includes a transparent conductive layer disposed upon a first surface of an electro-optic layer, a metallic layer disposed upon a second surface of the electro-optic layer, and a dielectric layer. The metallic layer has alternating grating and smooth regions; the smooth regions being of length near a multiple of an effective wavelength in the electro-optic layer of the light, and the grating regions has lines on a pitch near the effective wavelength.

In one embodiment, a method of sensing an electric field includes the steps of projecting a beam of plane-polarized light from a light source onto a plasmonic portion of a sensor, the plasmonic portion including an electro-optic layer and a metallic layer, converting a portion of the light into surface plasmons at a first grating region of the plasmonic portion, propagating the plasmons through a smooth region to a second grating region of the plasmonic portion, reflecting at least a portion of the plasmons from the second grating region back to the first grating region of the plasmonic portion, applying the electric field to the electro-optic layer, modulating reflected and scattered light as the electric field shifts the resonance wavelength of the plasmonic portion, and detecting and measuring reflected light from the plasmonic portion. The light is selected from the group consisting of visible and infrared light.

In one embodiment, a method of sensing a bioelectric field emitted by a mammal includes the steps of applying a garment to the mammal, the garment having a skinward surface and an outer surface, the garment further comprising a plurality of electric field sensors wherein each electric field sensor comprises a plasmonic portion, projecting plane-polarized light from light sources onto the plasmonic portions of the sensors, the plasmonic portions comprising an electro-optic layer and a metallic layer, converting a portion of the light into surface plasmons at first grating regions of the plasmonic portions of the sensors, propagating the plasmons through smooth regions to second grating regions of the plasmonic portions of the sensors, reflecting at least a portion of the plasmons from the second grating regions back to the first grating regions of the plasmonic portion, applying the electric field to the electro-optic layer of the sensors, modulating reflected light as the plasmons interact with the light and some plasmons reradiate as light at the first and second grating regions, detecting and measuring reflected and radiated light from the plasmonic portion. The light is selected from the group consisting of visible and infrared light.

In one embodiment, a surface-plasmon sensor includes a light source for emitting plane-polarized light having a free-space wavelength, a photodetector, and a plasmonic portion. The plasmonic portion includes a dielectric layer and a first layer having a first surface opposite a second surface. The first layer is formed of a material having a variable index of refraction and being one of a magneto-optic material, a thermo-optic material, and an acousto-optic material. A transparent conductive layer is disposed upon the first surface of the first layer, and a metallic layer is disposed upon the second surface of the first layer. The metallic layer has alternating grating and smooth regions. Each smooth region has a cavity length near a multiple of an effective wavelength of the light in the first layer, and each grating region has lines on a pitch near the effective wavelength.

DETAILED DESCRIPTION

Figure 1:
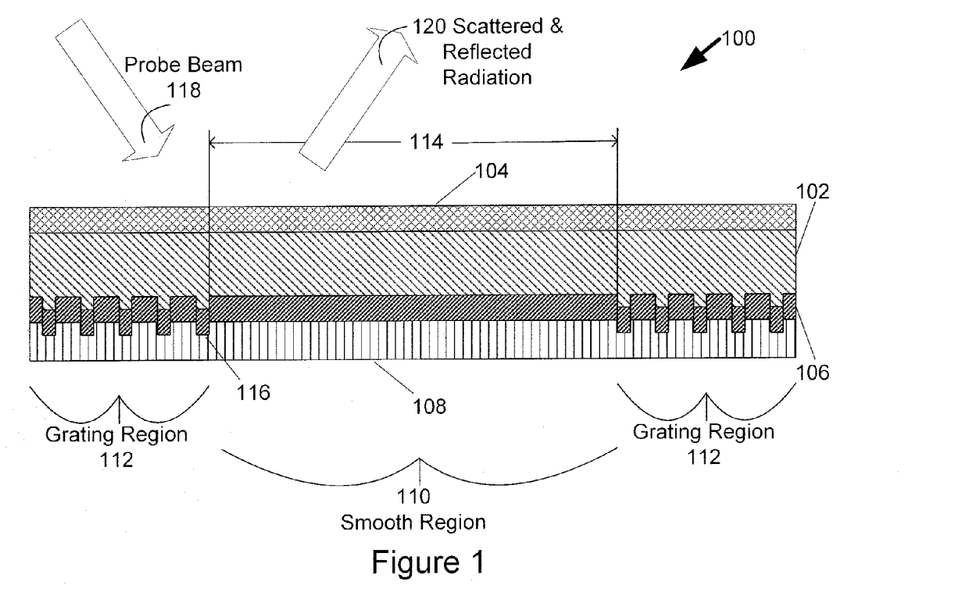
FIG. 1 is a cross section of a plasmonic portion of surface-plasmon electric field sensor.

FIG. 1 is a cross section of a plasmonic portion 100 of a surface-plasmon electric field sensor, according to one embodiment. This sensor has an electro-optic layer 102 of lithium niobate ($LiNbO_3$), preferably about one micron thick, having an index of refraction variable with applied electric field. On top of electro-optic layer 102 is a thin, approximately 100 nanometers, transparent ground electrode 104, which is for example also known as a transparent conductive layer 104, made of an indium tin oxide. Below electro-optic layer 102 is a thin, approximately 20 to 50 nanometers thick, layer of a metallic conductor 106 (also known as "metallic layer 106"), such as silver or gold. Gold is expected to work well at infrared wavelengths such as 1550 nanometers, while silver is preferred at optical wavelengths. Metallic layer 106 is coated with a protective insulating dielectric layer 108 (also known as "protective insulating layer 108") of titanium dioxide, for example.

While lithium niobate is preferred for the electro-optic layer because of its sensitivity, it is likely possible to build alternative embodiments having electro-optic layers made of other electro-optic materials known in the art such as Lithium Tantalate ($LiTaO_3$), Barium Titanate $BaTiO_3$, Strontium Titanate $SrTiO_3$, PLZT (Lanthanum doped Lead Zirconium Titanate $PbLaTiZrO_3$), KDP (Potassium DiPhosphate $KH_2PO_4$), or ADP (Ammonium DiPhosphate $NH_4H_2PO_4$).

Plasmonic portion 100 of the sensor of FIG. 1 may have additional layers, not shown, including one or more layers for scratch protection and passivation, metal layers to provide good electrical contact to the ground electrode, and the like. Such layers are well known to those skilled in the art.

Figure 2:
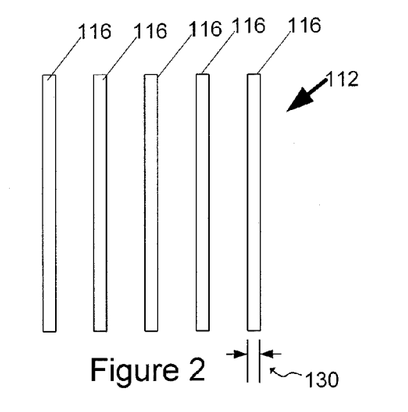
FIG. 2 is a surface layout diagram of a grating region of a first embodiment of the sensor.

With reference to FIGS. 1 and 2, plasmonic portion 100 of the sensor has at least one smooth region 110 flanked by multiple grating regions 112. The smooth region has length 114 (also known as "cavity length 114"), in an embodiment, of 2100 nanometers, equal to a multiple of a wavelength, such as two to five and preferably three wavelengths, to form a resonant cavity at a particular wavelength of electromagnetic radiation. Grating regions 112 have multiple parallel raised lines 116 on metallic layer 106 and electro-optic layer 102 surface, each line having a width 130 of approximately 175 nanometers. In an embodiment, these lines are raised by 40 to 50 nanometers, and each grating region 112 has from three to ten, preferably five, parallel lines spaced on a pitch of approximately 700 nanometers. This is approximately a one-wavelength pitch for light with a free space wavelength of 1550 nanometers because of the high coefficient of refraction of the lithium niobate electro-optic layer. In an embodiment, plasmonic portion 100 has many alternating smooth regions 110 and grating regions 112.

The transparent conductive layer 104 is electrically insulated from metallic layer 106, such that an applied voltage will develop an electric field in electro-optic layer 102. The sensor structure of FIG. 1 may be built on a substrate, not shown.

An alternative embodiment of the sensor has a thicker metallic layer 106, in the range 100 to 200 nanometers thick. In this embodiment, plasmons can appear only on the electro-optic side of the metal layer. In this embodiment, protective insulating layer 108 need not be a transparent material.

Plasmonic portion 100 of the sensor is interrogated by a probe beam 118 of polarized infrared light, in an embodiment this light is of free-space wavelength approximately 1550 nanometers. The light is polarized such that the electric field is perpendicular to the lines of grating regions 112. Since the refractive index of lithium niobate is about 2.5 at this free-space wavelength, the cavity length 114, formed as multiples of an effective wavelength of this light in the electro-optic layer, is about three wavelengths long. Some infrared light is trapped as surface plasmons, and some light is reflected (also known as "emitted, scattered and/or reflected light 120"), from plasmonic portion 100 of the sensor.

In one embodiment, electro-optic layer 102 is fabricated from an electro-optic polymer such as AJLS102/APC as described by Song et. Al. in Applied Physics Letters, 90, 191103 (2007). A wide range of electro-optic organic, chromophore doped, polymers are also possibilities for alternative embodiments. In another embodiment, grating region 112 has parallel incised lines on the metal and electro-optic layers instead of parallel raised lines 116.

Figure 3:
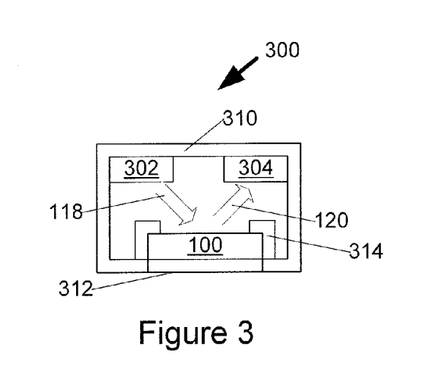
FIG. 3 is a schematic diagram of an embodiment having light source and light sensing at the sensor.

FIG. 3 is a schematic diagram of an embodiment having light source and light sensing at the sensor 300. A complete sensor 300 has a light emitting diode 302 (also known as "light source 302") and polarizing filter, or preferably a laser diode, that emits probe beam 118 onto plasmonic portion 100. A photodetector or photosensor 304, which may be a P-Intrinsic-N (PIN) photodiode, or alternatively, a phototransistor or even a photomultiplier tube, is positioned to receive at least some emitted, scattered and/or reflected light 120 from the plasmonic portion and to quantitatively measure that light. To minimize interference, sensor 300 is contained in a conductive case 310 having a nonconductive window 312 to admit electric fields to be sensed. At the top of plasmonic portion 100 of the sensor, transparent ground electrode 104 is bonded by conductive shielding 314 to conductive case 310.

Figure 4:
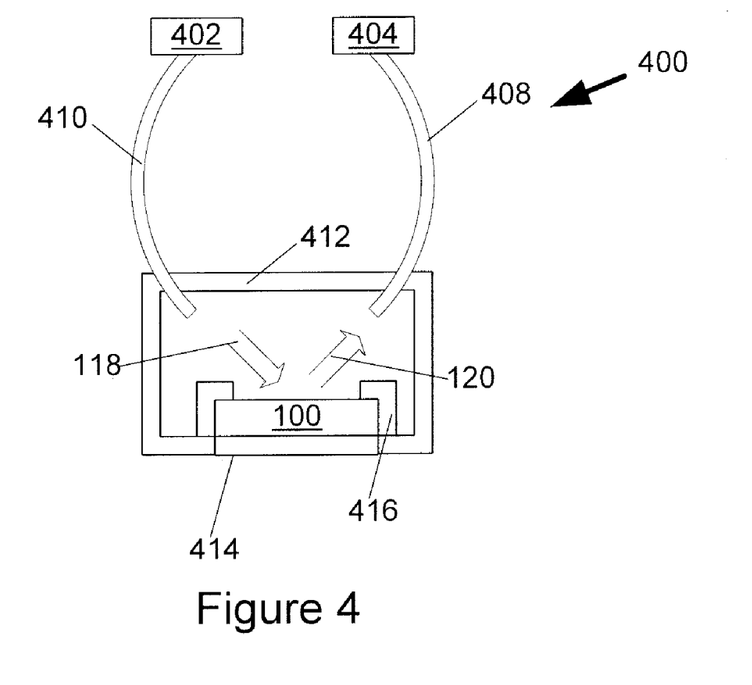
FIG. 4 is a schematic diagram of an embodiment having a remote light source and remote sensing to reduce electrical noise.

FIG. 4 is a schematic diagram of a complete sensor 400, in one embodiment. Light source 402, which may be a laser diode, and photosensor 404 are remotely located from plasmonic portion 100. In this embodiment, laser diode 402 emits infrared light into a fiberoptic fiber or bundle 410, which in turn emits probe beam 118 onto plasmonic portion 100. Similarly, reflected and/or scattered light 120 is received by a fiberoptic fiber or bundle 408 and directed to photosensor 404. Conductive case 412 has a nonconductive window 414 to admit electric fields to be sensed. At the top of plasmonic portion 100 of the sensor, transparent ground electrode 104 is bonded by conductive shielding 416 to the conductive case 412.

Figure 5:
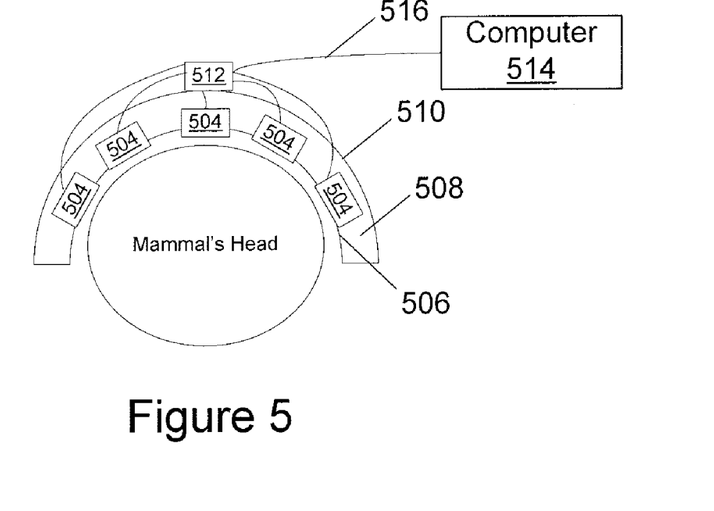
FIG. 5 is a schematic diagram of an electroencephalographic cap embodying the sensor.

FIG. 5 is a schematic diagram of an electroencephalographic cap embodying the sensor. In a medical application of the sensor, such as electroencephalography, an array of sensors 504 are attached to an inner, skinward, surface 506 of a garment such as a cap 508, with nonconductive windows (e.g., nonconductive window 312 of FIG. 3) facing inwards, towards the skin of, any mammal, such as a human, that may wear the garment. A layer 510 of the garment outside sensors 504 is made of a conductive material suitable for shielding electric fields such as copper mesh. Sensors 504 are connected to a sensor electronic module 512 which processes signals from photosensors of each sensor 504, and relays measurements, preferably using a wireless or infrared protocol 516, to a computer 514 for further processing and/or display.

In an alternative embodiment, sensors as depicted in FIG. 4 are used with the garment. In this embodiment, the plasmonic portion 100 of the sensors (e.g., sensor 504) is skinward of the layer of shielding conductive material, while the electronic portion of the sensors including light source 402 and photosensor 404 are outside the conductive material. In this embodiment, the electronic portions of the sensors may be located in the sensor electronics module 512.

Similarly, sensors 504 may be attached on the inner, skinward, surface of a socket for a prosthetic device, or on a skinward surface of a flexible vest or blanket for electrocardiography; with the socket, vest, or blanket, also having a conductive shielding (e.g., conductive shielding 314) layer outside the sensors 504. The garment may also have the form of a belt or strap. The garment may also be underwear for wear with a spacesuit or diving suit, or may be a spacesuit. The garment may be soft, elastic, and flexible or may be stiff, depending on the part of a body to which it is to be attached. The term garment as used herein therefore includes such caps, underwear, spacesuits, sockets, vests, straps, or blankets.

Figure 6:
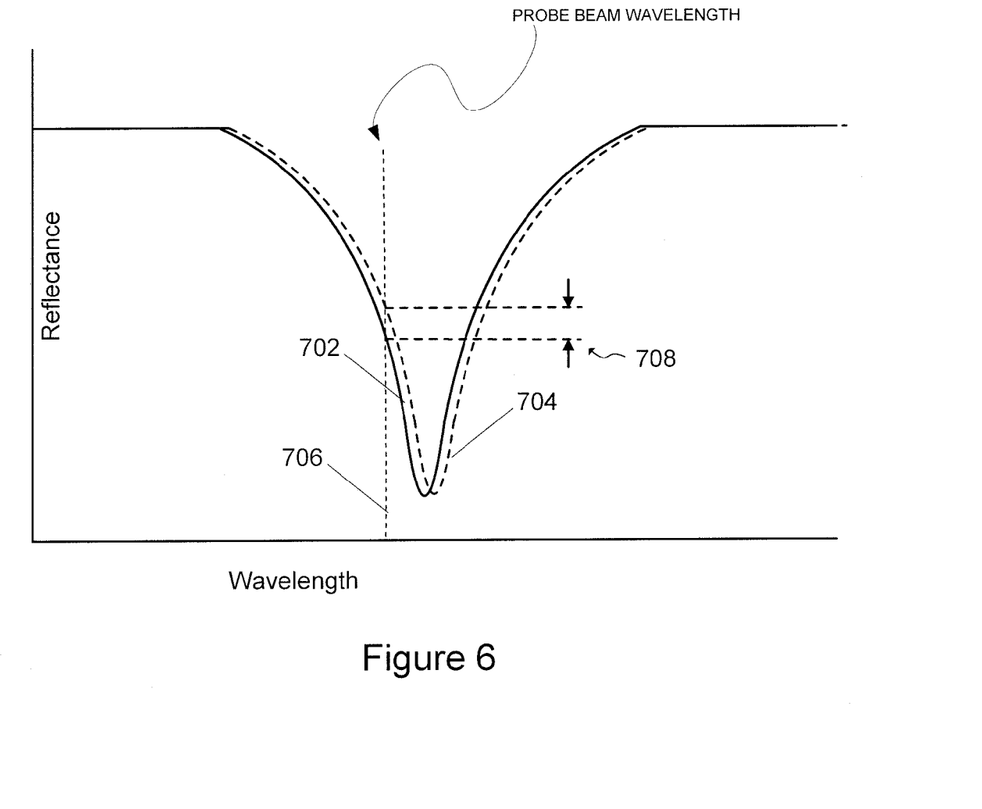
FIG. 6 is a graph illustrating changes of resonant absorption with electric field.

FIG. 6 is a graph illustrating changes of resonant absorption with electric field via light reflectance by plasmonic portion 100 of the sensor. There is a fairly sharp null (e.g., solid line 702 of FIG. 6) in reflectance at a particular "peak" wavelength determined by the spacing of lines in the grating regions and the width of the smooth region. FIG. 6 is a graph illustrating changes of resonant absorption with electric field. In the presence of an electric field, shifts in the coefficient of refraction of the electro-optic layer cause this "peak" wavelength to shift, (e.g., dashed line 704 of FIG. 6). The interrogation or probe beam wavelength is centered on a wavelength 706 on one side of the peak, such that reflectance of the probe beam changes 708 as the electric field changes.

Probe beam (e.g., probe beam 118) therefore has freespace wavelength near, within a few percent of, but not quite at, the free space null wavelength. The null wavelength being determined by factors including the index of refraction of electro-optic layer (e.g. electro-optic layer 102), width of the smooth region (e.g., smooth region 110) and spacing of lines in the grating regions (e.g., grating regions 112).

It is expected that the change in null wavelength with applied electric field will be greater than in most prior sensors because of the increased length of resonant path afforded by the cavity resonator formed by smooth regions (e.g., smooth region 110) and reflecting grating regions (e.g., grating regions 112).

While dimensions herein are described in context of a device built for operation at an infrared wavelength of 1550 nanometers, sensors as herein described may be designed to operate at other wavelengths including visible wavelengths. Operation at a particular chosen wavelength requires that light source 302 provide adequate illumination at that wavelength, that photosensor 304 be suitable for operation at that wavelength, metallic layer 106 be at least partially reflective at that wavelength, grating regions 112 be designed to have line spacing suitable for operation at that wavelength, electro-optic layer 102 be of a material transparent and electro-optic at that wavelength, and that the smooth regions be spaced apart by a multiple of that wavelength In the flowchart of FIG. 7, we see how a garment having the described sensors may be used to sense bioelectrical fields such as electroencephalographic, electromyographic, or electrocardiographic fields. The method 800 of FIG. 7 begins with step 802 by placing the garment on a human patient, (or dressing the patient in), the garment. The method is applicable to use with other mammals as well as humans. As heretofore described with reference to FIG. 5, the garment has a skinward inside surface 506 and an outer surface 510, the garment having multiple electric field sensors 504 each having a plasmonic portion 100.

Figure 7:
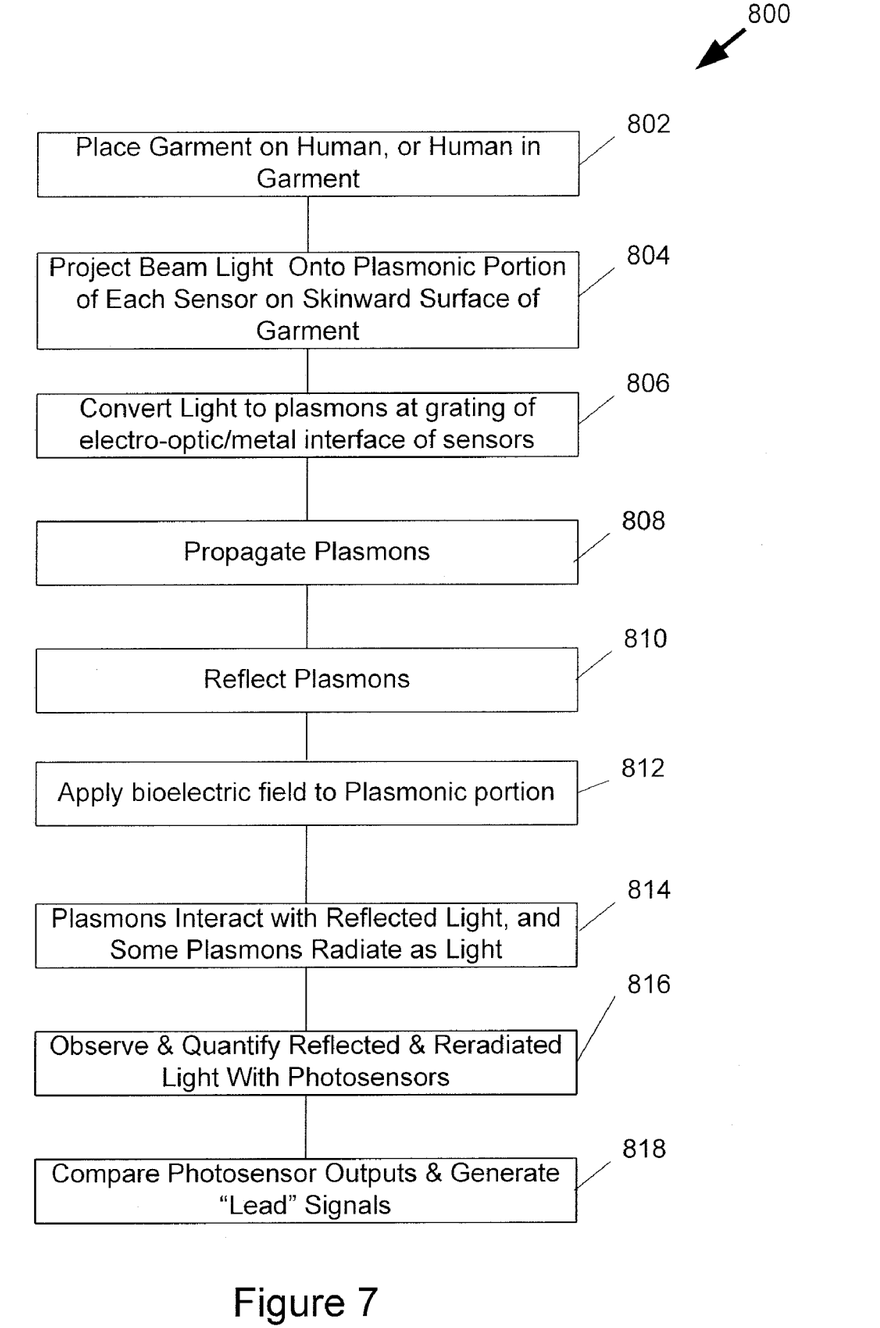
FIG. 7 is a flowchart illustrating how a garment having the described sensors may be used to sense bioelectrical fields such as electroencephalographic or electrocardiographic fields.

In step 804, Plane-polarized light is then projected from one or more light sources onto plasmonic portions 100 of the sensors 504, the plasmonic portions as heretofore described with reference to FIG. 1.

In step 806, some of the light incident on plasmonic portions 100 is converted into surface plasmons at first grating regions 112 of electro-optic layer 102 to metallic layer 106 of plasmonic portions 100 of each of the sensors 504. Method 800 continues with step 808 where these plasmons then propagate through smooth regions 110 to second grating regions 112 of plasmonic portions 100 of the sensors 504. In step 810, at the second grating regions 112, at least a portion of the plasmons are reflected from the second grating regions back towards the first grating regions 112 of the plasmonic portions.

In step 812, the bioelectric field from the human or other mammal is applied to the electro-optic layer of the sensors by allowing it to penetrate to metallic layer 106 of each sensor, and grounding the transparent conductive layer 104 of the plasmonic portions (e.g., plasmonic portion 100).

Some light incident on the plasmonic portions reflects 814, the amount of this light changes as the plasmons interact with the light at grating regions 112. Further, in step 814, some plasmons re-radiate as light at the first and second grating regions 112.

In step 816, scattered, reflected and radiated light from the grating regions is observed and quantified by photosensors 304 of the sensors 504. The reflected and radiated light from the grating regions will change slightly as the electric field changes.

Method 800 ends with step 818, where photosensor 304 outputs are then compared to produce individual "lead" signals corresponding to the traditional leads of an electrocardiogram, or to the traditional leads of an electroencephalogram.

It is anticipated that a magnetic field sensor may be fabricated by substituting a layer of a magneto-optic material for electro-optic layer 102 of the plasmonic portion of the sensor. Similarly, a temperature sensor may be fabricated by substituting a layer of a thermo-optic material for electro-optic layer 102 of the plasmonic portion of the sensor. Similarly, a pressure sensor may be fabricated by substituting a layer of an acousto-optic material for electro-optic layer 102 of the plasmonic portion of the sensor.

While the forgoing has been particularly shown and described with reference to particular embodiments thereof, it will be understood by those skilled in the art that various other changes in the form and details may be made without departing from the spirit and hereof. It is to be understood that various changes may be made in adapting the description to different embodiments without departing from the broader concepts disclosed herein and comprehended by the claims that follow.

What is claimed is:

1. A surface-plasmon electric field sensor, comprising:
   a light source for emitting plane-polarized light having a free-space wavelength;
   a photodetector; and
   a plasmonic portion comprising:
      an electro-optic layer having a first surface opposite a second surface,
      a transparent conductive layer disposed upon the first surface of the electro-optic layer,
      a metallic layer disposed upon the second surface of the electro-optic layer, and
      a dielectric layer;
   wherein the metallic layer has alternating grating and smooth regions, each smooth region having a cavity length near a multiple of an effective wavelength of the light in the electro-optic layer, and each grating region having lines on a pitch near the effective wavelength.

2. The sensor of claim 1, wherein the light source comprises an infrared laser diode.

3. The sensor of claim 2, wherein the light source operates at a wavelength near 1550 nanometers.

4. The sensor of claim 1, wherein the dielectric layer is transparent to the light, and wherein the metallic layer is between 20 and 50 nanometers thick.

5. The sensor of claim 4, wherein each smooth region has a cavity length of between two and five effective wavelengths of the light in the electro-optic layer.

6. The sensor of claim 5, wherein each grating region comprises between three and ten parallel lines spaced near the effective wavelength of the light in the electro-optic layer.

7. The sensor of claim 5, wherein the electro-optic layer comprises an electro-optic dielectric material selected from the group consisting of Lithium Niobate, Lithium Tantalate ($LiTaO_3$) Barium Titanate $BaTiO_3$, Strontium Titanate $SrTiO_3$, PLZT (Lanthanum doped Lead Zirconium Titanate $PbLaTiZrO_3$), KDP (Potassium DiPhosphate $KH_2PO_4$), and ADP (Ammonium DiPhosphate $NH_4H_2PO_4$).

8. The sensor of claim 5, wherein the electro-optic layer comprises an electro-optic polymer.

9. The sensor of claim 1, wherein the transparent conductive layer is grounded.

10. The sensor of claim 1, further comprising a first fiberoptic for directing light from the light source to the plasmonic portion, and a second fiberoptic for directing light from the plasmonic portion to the photodetector.

11. The sensor of claim 1, wherein the light source provides visible light.

12. A garment having a skinward side and an outside side, the garment having a plurality of sensors disposed to sense electric fields at the skinward side of the garment, each sensor comprising:
   a light source for emitting plane-polarized light having a free-space wavelength;
   a photodetector; and
   a plasmonic portion comprising:
      an electro-optic layer having a first surface opposite a second surface,
      a transparent conductive layer disposed upon the first surface of the electro-optic layer,
      a metallic layer disposed upon the second surface of the electro-optic layer, and
      a dielectric layer;
   wherein the metallic layer has alternating grating and smooth regions, each smooth region having a cavity length near a multiple of an effective wavelength of the light in the electro-optic layer, and each grating region having lines on a pitch near the effective wavelength.

13. The garment of claim 12, wherein the garment is selected from the group consisting of a cap, a vest, a blanket, a strap, underwear, and the stump-socket of a prosthetic device; and wherein the garment is intended for wear by a human.

14. The garment of claim 13, wherein each of the smooth regions has a cavity length of between two and five effective wavelengths of the light in the electro-optic layer.

15. The garment of claim 14, wherein each grating region comprises between three and ten parallel lines spaced near the effective wavelength of the light in the electro-optic layer.

16. The garment of claim 15, wherein the electro-optic layer comprises Lithium Niobate.

17. The garment of claim 15, wherein the electro-optic layer comprises an electro-optic polymer.

18. The garment of claim 13, wherein the garment further comprises a conductive layer outside at least the plasmonic portion of the sensors, the conductive layer for shielding the sensors from external electric fields.

19. The garment of claim 18, wherein the light source is an infrared laser diode operating at a free-space wavelength near 1550 nanometers.

20. The garment of claim 18, wherein the dielectric layer is transparent to the light, and wherein the metallic layer is between 20 and 50 nanometers thick.

21. The garment of claim 18, wherein the light source and the photodetector of each sensor are located outside the layer of conductive material, and wherein the light source and the photodetector are coupled to the plasmonic portion of each sensor with fiberoptic fibers.

22. A method of sensing an electric field comprising:
projecting a beam of plane-polarized light from a light source onto a plasmonic portion of a sensor, the plasmonic portion comprising an electro-optic layer and a metallic layer;
converting a portion of the light into surface plasmons at a first grating region of the plasmonic portion;
propagating the plasmons through a smooth region to a second grating region of the plasmonic portion;
reflecting at least a portion of the plasmons from the second grating region back to the first grating region of the plasmonic portion;
applying the electric field to the electro-optic layer;
modulating reflected and scattered light as the electric field shifts the resonance wavelength of the plasmonic portion;
detecting and measuring reflected light from the plasmonic portion; and
wherein the light is selected from the group consisting of visible and infrared light.

23. The method of claim 22, wherein the smooth region has a cavity length of between two and five effective wavelengths of the light in the electro-optic layer; and wherein each of the grating regions comprises between three and ten parallel lines spaced near the effective wavelength.

24. A method of sensing a bioelectric field emitted by a mammal, comprising:
applying a garment to the mammal, the garment having a skinward surface and an outer surface, the garment further comprising a plurality of electric field sensors wherein each electric field sensor comprises a plasmonic portion;
projecting plane-polarized light from light sources onto the plasmonic portions of the sensors, the plasmonic portions comprising an electro-optic layer and a metallic layer;
converting a portion of the light into surface plasmons at first grating regions of the plasmonic portions of the sensors;
propagating the plasmons through smooth regions to second grating regions of the plasmonic portions of the sensors;
reflecting at least a portion of the plasmons from the second grating regions back to the first grating regions of the plasmonic portions of the sensors;
applying the bioelectric field to the electro-optic layer of the sensors;
modulating reflected light as the plasmons interact with the light and some plasmons reradiate as light at the first and second grating regions;
detecting and measuring reflected and radiated light from the plasmonic portions of the sensors; and
wherein the light is selected from the group consisting of visible and infrared light.

25. The method of claim 24, wherein each of the smooth regions has a cavity length of between two and five effective wavelengths of the light in the electro-optic layer; and wherein each of the grating regions comprises between three and ten parallel lines spaced near the effective wavelength.

26. The method of claim 24, wherein the mammal is human.

27. The method of claim 26, wherein the bioelectric fields are electroencephalographic.

28. The method of claim 26, wherein the bioelectric fields are electromyographic.

29. The method of claim 26, wherein the bioelectric fields are electrocardiographic.

30. A surface-plasmon sensor, comprising:
a light source for emitting plane-polarized light having a free-space wavelength;
a photodetector; and
a plasmonic portion comprising:
a first layer having a first surface opposite a second surface, the first layer being formed of a material having a variable index of refraction and selected from the group consisting of a magneto-optic material, a thermo-optic material, and an acousto-optic material,
a transparent conductive layer disposed upon the first surface of the first layer,
a metallic layer disposed upon the second surface of the first layer, and
a dielectric layer;
wherein the metallic layer has alternating grating and smooth regions, each smooth region having a cavity length near a multiple of an effective wavelength of the light in the first layer, and each grating region having lines on a pitch near the effective wavelength.

* * * * *